United States Patent [19]
Cohen et al.

[11] Patent Number: 6,073,767
[45] Date of Patent: Jun. 13, 2000

[54] PACKAGE AND METHOD TO REDUCE BACTERIAL CONTAMINATION OF STERILIZED ARTICLES

[75] Inventors: Bernard Cohen, Berkeley Lake; Julie R. Taylor, Snellville, both of Ga.

[73] Assignee: Kimberly-Clark Worldwide, Inc., Neenah, Wis.

[21] Appl. No.: 09/086,109

[22] Filed: May 29, 1998

[51] Int. Cl.$^7$ .................................................. B65D 83/10
[52] U.S. Cl. ...................... 206/363; 206/460; 206/484.1; 206/815
[58] Field of Search .................................. 206/439, 363, 206/484.1, 460, 484, 815; 383/35; 220/260

[56] References Cited

U.S. PATENT DOCUMENTS

| | | |
|---|---|---|
| D. 259,997 | 7/1981 | Porteous . |
| 2,552,870 | 5/1951 | Scherer . |
| 3,270,878 | 9/1966 | Giesler ..................................... 206/484 |
| 3,527,400 | 9/1970 | Shepherd et al. ........................ 206/439 |
| 3,618,756 | 11/1971 | Trewella . |
| 3,698,549 | 10/1972 | Glassman . |
| 3,717,244 | 2/1973 | Smith . |
| 3,754,700 | 8/1973 | Bonk . |
| 3,761,013 | 9/1973 | Schuster . |
| 3,926,311 | 12/1975 | Laske . |
| 3,938,659 | 2/1976 | Wardwell . |
| 3,991,881 | 11/1976 | Augurt ..................................... 206/363 |
| 3,995,739 | 12/1976 | Tasch et al. . |
| 4,097,236 | 6/1978 | Daly et al. ............................ 206/484.1 |
| 4,121,714 | 10/1978 | Daly et al. . |
| 4,146,133 | 3/1979 | Bogorad et al. . |
| 4,177,620 | 12/1979 | Daley et al. . |
| 4,194,622 | 3/1980 | Lewis . |
| 4,215,682 | 8/1980 | Kubik et al. . |
| 4,276,982 | 7/1981 | Sibrava et al. . |

(List continued on next page.)

FOREIGN PATENT DOCUMENTS

| | | |
|---|---|---|
| 0 454 104 | 10/1991 | European Pat. Off. . |
| 1447984 | 6/1966 | France . |
| 2 317 354 | 10/1974 | Germany . |
| 56-21619 | 2/1981 | Japan . |
| 1 459 590 | 12/1976 | United Kingdom . |
| 79/00590 | 8/1979 | WIPO . |
| 96/37276 | 11/1996 | WIPO . |
| 97/04155 | 2/1997 | WIPO . |
| 97/21364 | 6/1997 | WIPO . |
| 98/02302 | 1/1998 | WIPO . |

OTHER PUBLICATIONS

Abstract for Japanese 07 213831 A.
Abstract for Japanese 04 305213 A.
Abstract for Japanese 06 218211 A.
Abstract for Japanese 05 214655 A.
Abstract for French 1,447,984.
Abstract for German 2 317 354.
Abstract for Japanese 56–21619.
Copy of PCT Search Report mailed Sep. 28, 1999.

*Primary Examiner*—M. D. Patterson
*Assistant Examiner*—Nuan T. Lam
*Attorney, Agent, or Firm*—Nancy M. Klembus

[57] ABSTRACT

Disclosed is a peel pouch adapted to enclose an article to be sterilized, the peel pouch having a base panel having an exterior surface and an edge. In selected embodiments, a first and a second flap are disposed along the edge of the base panel so that the first flap is spaced apart from the second flap. The peel pouch further includes a cover panel having at least one tab disposed on along an edge of the cover panel, the cover panel overlying the base panel. In some embodiments, at least a portion of the tab is disposed above and between the first and second flaps. At least one seal joins the cover panel to the base panel so that a pocket suitable to receive articles to be sterilized is formed. The peel pouch may be electret treated prior to insertion of the article to be sterilized. During opening of the peel pouch, the exterior surface of the base panel is held against a supporting surface while a separating force is applied to the tab of the cover panel to separate the cover panel from the base panel.

19 Claims, 2 Drawing Sheets

U.S. PATENT DOCUMENTS

| | | |
|---|---|---|
| 4,352,429 | 10/1982 | Newman . |
| 4,358,015 | 11/1982 | Hirsch . |
| 4,375,718 | 3/1983 | Wadsworth et al. . |
| 4,513,049 | 4/1985 | Yamasaki et al. . |
| 4,588,537 | 5/1986 | Klaase et al. . |
| 4,592,815 | 6/1986 | Nakao . |
| 4,714,595 | 12/1987 | Anthony et al. . |
| 4,874,090 | 10/1989 | Dyke . |
| 5,071,686 | 12/1991 | Genske et al. . |
| 5,110,620 | 5/1992 | Tani et al. . |
| 5,178,277 | 1/1993 | Brown et al. ............ 206/439 |
| 5,342,673 | 8/1994 | Bowman et al. . |
| 5,358,791 | 10/1994 | Johnson . |
| 5,401,446 | 3/1995 | Tsai et al. . |
| 5,418,022 | 5/1995 | Anderson et al. ............ 428/35.2 |
| 5,459,978 | 10/1995 | Weiss et al. . |
| 5,616,408 | 4/1997 | Oleszczuk et al. . | ns and fungi that can cause serious, and sometimes
PACKAGE AND METHOD TO REDUCE BACTERIAL CONTAMINATION OF STERILIZED ARTICLES

FIELD OF THE INVENTION

The present invention relates generally to peel pouches and methods utilizing peel pouches.

BACKGROUND OF THE INVENTION

Various articles such as medical instruments and supplies which are used in hospitals are subjected to sterilization treatments such as, for example, steam sterilization, ethylene oxide gas sterilization, radiation sterilization, chemical sterilization and dry-heating sterilization prior to such use. The sterilization of such articles and maintenance of such articles in a sterilized condition is important to prevent hospital-acquired infections, also known as noscomial infections, in hospital patients. During a hospital stay, patients may be exposed to the illnesses of other patients, including viruses, bacteria, and fungi that can cause serious, and sometimes deadly, diseases. While exposing a healthy person to these illnesses may cause serious concerns, the problem is compounded by the ill health of the patients who are exposed to these additional diseases. Thus, the sterilization and maintenance of such articles in a sterile condition until use is highly important.

In many instances, non-sterile articles such as instruments and supplies are packaged prior to sterilization in what is conventionally called a "peel pack." The pack and its contents are then subjected to sterilizing conditions. One of the major functions of the peel pack is to maintain the sterilized articles in a sterile condition until such time as the articles are utilized.

Typically, there are three elements to a peel pack. The pack includes a first sheet or layer of a material which is impervious to pathogens. Exemplary materials of this sort are polyolefinic films or plastics. In some instances, the films or plastic materials are molded to provide a chamber for retention of the articles. Another element of a peel pack is an adhesive which is usually applied around the outer periphery of the pathogen impervious layer. Peel pouches also include a second sheet of a material (typically paper) which allows entry of sterilizing gases into the chamber of the peel pouch during a sterilization procedure but prohibits entry of pathogens into the chamber thereafter. This second sheet of paper or other suitable material is joined to the pathogen impervious sheet or layer by the adhesive to form the peel pouch. It should be noted that, in some instances, the second sheet can be heat sealed directly onto the pathogen impervious sheet or layer. These situations typically arise where the pathogen impervious sheet or layer has been specially formulated to heat seal with a paper sheet. In such instances, the necessity of an adhesive is eliminated.

An article to be sterilized is placed between the two layers or sheets or, if present, within the chamber of the pouch and the periphery of the pouch is completely sealed. The peel pouch and the article contained therein are then sterilized by any one of a variety of methods. During sterilization, the sterilant enters the peel pouch through the second sheet and sterilizes the article contained therein. After sterilization, the first and second sheets do not permit reintroduction of bacteria and other contaminants into the chamber of the pouch.

Conventionally, peel pouches are opened by peeling the paper sheet away from the pathogen impervious sheet or layer to allow access to the articles contained therebetween.

Articles which are sterilized in peel pouches can be contaminated by bacteria upon extraction of the article from the pouch. One way this contamination occurs is during opening of the peel pouch. The movement of the pouch during opening may cause some of the bacteria or other contaminants on the exterior surfaces of the pouch to become airborne and come to rest on the sterilized surfaces of the article which was just removed from the peel pouch. As some peel pouches do not always open easily and cleanly, this becomes a more significant concern. The spreading of the contaminants from the exterior surfaces of the peel pouch to sterilized articles and the like increases the opportunities for noscomial infections.

DEFINITIONS

As used herein, the term "dielectric material" refers to any material, such as a polymer, which is an electrical insulator or in which an electric field can be sustained with a minimum dissipation of power. A solid material is a dielectric if its valence band is full and is separated from the conduction band by at least 3 eV. See, for example, the *McGraw-Hill Encyclopedia of Science and Technology*, 7th Edition, copyright, 1992, which is hereby incorporated by reference.

As used herein, the term "Kraft" paper is a paper which is manufactured from pulp or fibers produced by conventional Kraft pulping processes. This alkaline pulping process typically uses a combination of sodium hydroxide and sodium sulfide. The term Kraft is derived from the German word meaning "strong" because Kraft pulp is among the stronger chemical pulps. Those of skill in the art utilize the term "sulfate pulping" alternatively or as a synonym for Kraft pulping. The "Handbook for Pulp & Paper Technologists" by Gary A. Smook (Angus Wilde Publications), copyright 1992, [ISBN 0-9694628-1-6] gives a detailed description of conventional Kraft pulping techniques at, for example, chapter 7, pages 74–83. The entirety of this book is hereby incorporated by reference.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometric configurations of the material. These configurations include, but are not limited to, isotactic, syndiotactic and random symmetries.

As used herein, the terminology "electret treatment" or "electreting" refers to any process which places a charge in and/or on a dielectric material. One exemplary process for placing a charge on a dielectric material involves the application of DC corona discharge to the material. An exemplary conventional method of this type is described in detail in U.S. Pat. No. 5,401,446 to Tsai et al. entitled "Method and Apparatus for the Electrostatic Charging of a Web or Film" which issued on Mar. 28,1995, the entirety of which is hereby incorporated by reference.

As used herein, any given range is intended to include any and all lesser included ranges. For example, a range of from 45–90 would also include the ranges of from 50–90, 45–30, 46–89, etc.

As used herein, the term "comprising" is synonymous with "including," "containing," or "characterized by," is inclusive or open-ended and does not exclude additional, unrecited elements or method steps.

SUMMARY OF THE INVENTION

In response to the foregoing problems and difficulties encountered by those of skill in the art, the present invention is directed to a product configured to reduce the opportunities for contaminants on the exterior surface of the peel pouch to contaminate the sterile item within the pouch during and after opening of the pouch. The peel pouch includes a base panel having an exterior surface and an edge. The peel pouch also includes a cover panel having at least one tab disposed along an edge of the cover panel. The cover panel is positioned so that it overlies the base panel. In selected embodiments, the base panel further includes a first and a second flap which are disposed along the edge of the base panel so that the first flap is spaced apart from the second flap. In alternate embodiments, a single flap may be utilized. In those embodiments having first and second flaps along the edge of the base panel, at least a portion of the tab is disposed above and between the first and second flaps.

In selected embodiments, the cover panel may be manufactured from a dielectric material such as, for example, polyolefins, polyesters and nylon. The cover panel may also be formed of a non-dielectric material coated with a dielectric material, or the like. The cover panel may be electret treated to enhance the retention of contaminants on the exterior surface of the cover panel. Likewise, the base panel may be manufactured from a dielectric material such as, for example, spun polyolefins such as, for example, TYVEK® or other breathable films. The base panel may also be formed of a non-dielectric material such as, for example, Kraft paper which may, in selected embodiments, be coated with a dielectric material. The base panel may then be electret treated to enhance the retention of contaminants on the exterior surface of the base panel.

A seal is formed to join the cover panel to the base panel so that a pocket suitable to receive articles to be sterilized is formed. Once the article is placed within the pocket, the pocket is sealed completely shut.

After sterilization of the article and the peel pouch, the peel pouch may be opened by holding the exterior surface of the base panel against a supporting surface by applying a securing force to the base panel along the edge and/or the flaps. A separating force may then be applied to the tab of the cover panel, drawing the cover panel away from the base panel. Thus, the cover panel is separated from the base panel and the article that was contained within the peel pouch may be removed. During opening, the contaminants on the exterior of the base panel are trapped between the base panel and the supporting surface. The contaminants on the exterior of the cover panel are directed away from the article. Because the base panel and, thus, the article stay relatively stationary during opening of the pouch, the potential for contamination of the sterilized article is further reduced.

The method of the present invention includes the step of providing a peel pouch having a base panel with an interior surface, an exterior surface and an edge. In selected embodiments, a first and second flap are disposed along the edge of the base panel so that the first flap is spaced apart from the second flap. The peel pouch also includes a cover panel with an interior surface, an edge, and a tab disposed along the edge of the cover panel, the cover panel overlaying the base panel so that the interior surface of the base panel is adjacent to the interior surface of the cover panel. In selected embodiments, the tab of the cover panel is positioned between the first and second flaps of the base panel. The base panel is secured to the cover panel by a seal, forming a pocket into which an article to be sterilized may be placed.

In some embodiments, at least a portion of the peel pouch is subjected to electret treatment. In selected embodiments, the cover panel is a dielectric material and is subjected to electret treatment. In other embodiments, the base panel is a dielectric material and is subjected to electret treatment. In still other embodiments, both the cover panel and base panel are subjected to electret treatment.

A medical article to be sterilized is placed within the chamber of the peel pouch and the peel pouch is sealed. The peel pouch and the medical article are exposed to a sterilization cycle.

During opening of the peel pouch, the exterior surface of the base panel of the peel pouch is placed against a supporting surface. A securing force is applied to the base panel to hold the exterior surface of the base panel against the supporting surface. A separating force is then applied to the tab of the cover panel to separate the cover panel from the base panel.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Figure 1:
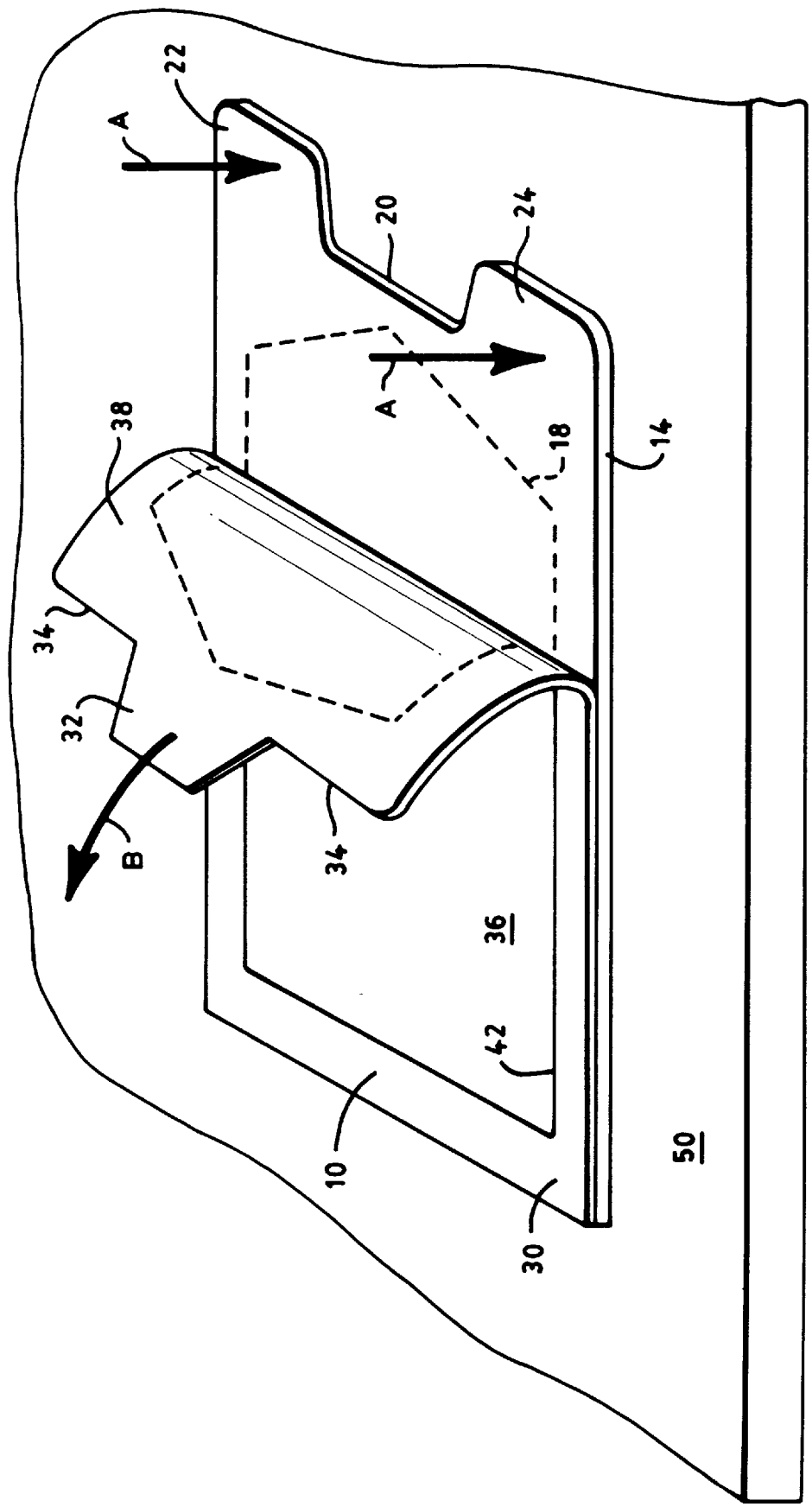
FIG. 1 is a top perspective view of an embodiment of the peel pouch of the present invention.
Figure 2:
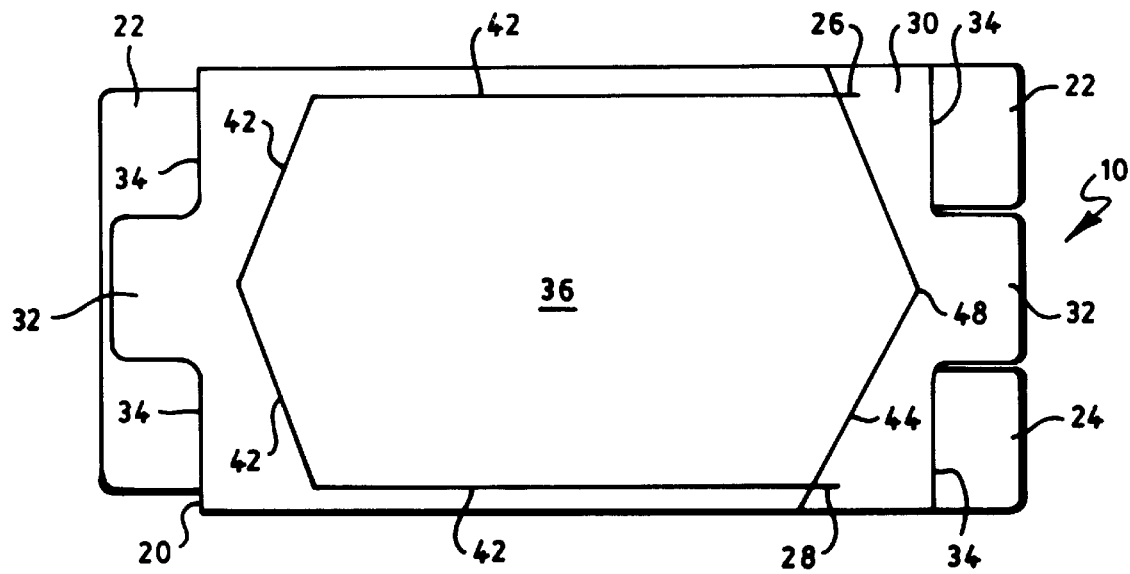
FIG. 2 is a top plan view of an another embodiment of the peel pouch of the present invention.
Figure 3:
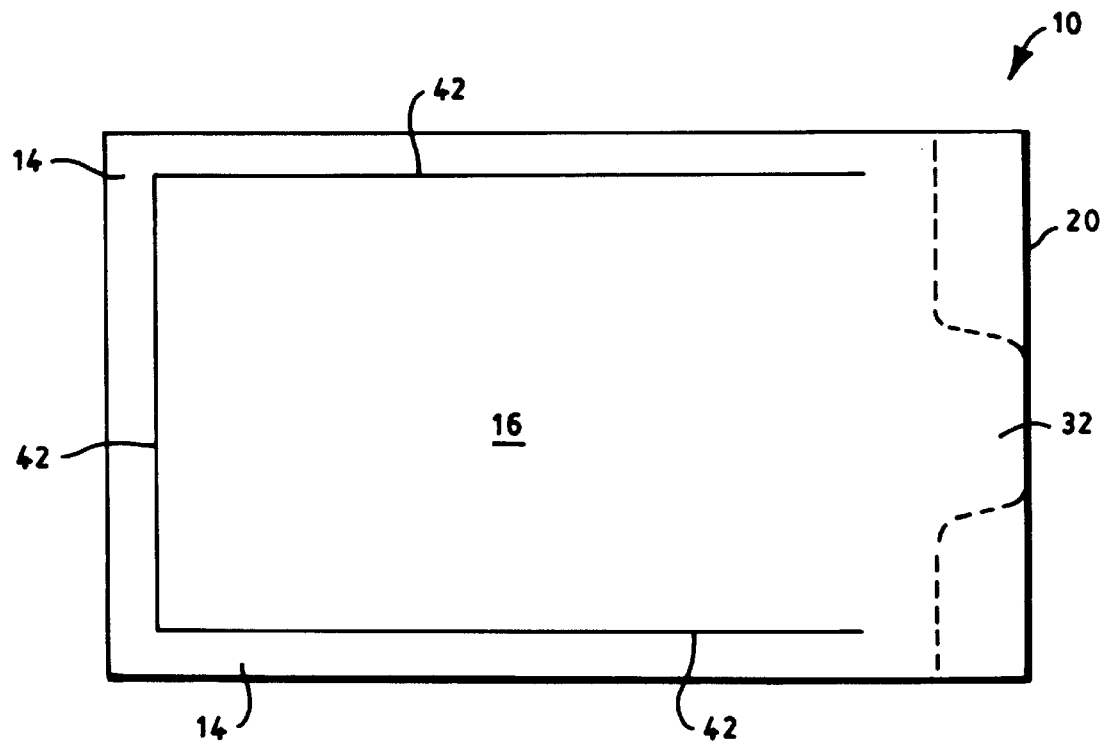
FIG. 3 is a bottom plan view of yet another alternate embodiment of the peel pouch of the present invention.

In response to the foregoing challenges which have been experienced by those of skill in the art, the present invention is directed toward a peel pouch 10 which assists in preventing contaminants on the exterior surface of the peel pouch 10 from becoming airborne during opening of the peel pouch 10 and contaminating the sterile article being removed from the peel pouch. As shown in FIGS. 1–3, the peel pouch 10 of the present invention, shown in FIG. 1 on a supporting surface 50, includes a base panel 14 having an exterior surface 16 (FIG. 3), an interior surface 18 and an edge 20. In the embodiment depicted in FIG. 1, two flaps 22 and 24 are positioned along the edge 20 of the base panel 14. The flaps 22 and 24 are preferably spaced apart from each other. Such a configuration is also shown on the right side of the embodiment depicted in FIG. 2.

As best shown in FIGS. 1 and 2, a cover panel 30 having an exterior surface 36, an interior surface 38, and an edge 34 overlies the base panel 14 so that the interior surface 38 of the cover panel 30 is facing the interior surface 18 of the base panel 14. Positioned along the edge 34 of the cover panel 30 is a tab 32. In selected embodiments and as shown in FIGS. 1 and 2, at least a portion of the tab 32 of the cover panel 30 is positioned between the flaps 22 and 24 of the base panel 14.

As best shown in FIG. 2, a seal 42 extends generally along three sides of the peel pouch 10 to seal the cover panel 30 to the base panel 14. A pocket 46, best shown in FIG. 1, is formed by this seal 42 so that articles (not shown) which are to be sterilized may be placed within the pocket 46. The seal 42 may be formed conventionally by any of a variety of methods, including adhesive sealing, heat sealing and the like. After an article is placed within the pocket 46, the seal 44 is also formed conventionally by adhesive sealing, heat sealing or the like. The seal 44 in cooperation with the seal 42 completely close the pocket 46 and enclose the article therein.

The seals 42 and 44 must be sufficiently durable to maintain sterility of the articles during the sterilization process and handling of the sterilized pouch 10, but sufficiently frangible to enable the panels 14 and 30 of the pouch to be separated and the sterilized article removed from the pocket 46 without significant effort. To assist in the identification of the article enclosed within the pocket 46, the cover panel 30 and/or the base panel 14 may be transparent.

After securing an article (not shown) within the peel pouch 10, the peel pouch and article are sterilized in a conventional manner. The base and cover panels 14 and 30, respectively, do not permit reentry of contaminants into the pocket 46 of the peel pouch 10 as long as the pouch remains sealed. Thus, the article contained therein will remain sterilized until the peel pouch 10 is opened. The manner in which the peel pouch is opened is important to maintaining the sterility of the article contained therein.

FIG. 1 shows the peel pouch 10 of the present invention as the peel pouch is being opened. The peel pouch 10 is placed on the support surface 50 so that the exterior surface 16 of the base panel 14 is placed against the support surface 50. The flaps 22 and 24 are held down by a securing force as indicated by the arrows marked A in FIG. 1. Such a force may be applied by the thumb and forefinger of a user's hand. The tab 32 is grasped by the other hand of the user and a separating force is applied to the tab 32, the separating force being indicated by the arrow marked B. The separating force pulls the cover panel 30 away from the base panel 14 and breaks at least the seal 44, and possibly a portion of the seal 42. The centrally positioned tab 32 inhibits tearing of the cover panel during opening because the separating force is focused from the tab 34 downward to the seal 44.

The seal 44 may be configured to assist the separating force in cleanly and simply opening the peel pouch 10. For example, the seal 44 depicted in FIG. 2 is angled outwardly from a center point 48 away from the edge 34 and toward the ends 26 and 28 of the seal 42. A variety of other configurations of the seal 44 may be used in the present invention so long as the pouch is configured to force the separation force from tab 32 toward the seal 44.

During separation of the cover panel 30 and base panel 14, contaminants on the base panel 14 which are easily dislodged from the base panel are trapped between the surface 50 and the base panel 14. The contaminants on the exterior surface 36 of the cover panel 30 are directed away from the article (not shown) which is contained within the pocket 46. Because the peel pouch 10 has been positioned on the surface 50 and the base panel 14 has been held in a stationary position relative to the surface 50, the sterilized article has a reduced tendency to move about with respect to the pouch during opening of the pouch, and thus will be less likely to contact the contaminated edges or surfaces of the peel pouch 10 or the surface 50.

In selected embodiments, the base panel 14 may be formed of a material which allows the entry of sterilizing gases such as, for example, cellulosic materials such as paper and, in particular, Kraft paper, into the pocket 46 of the peel pouch. The material from which the base panel 14 may be formed may also be a dielectric material such as, for example, a spun polyolefin such as TYVEK® or a breathable film. The cover panel 30 may be formed of a dielectric material such as a polyolefin, polyester or nylon, although other suitable dielectric materials may also be used. The cover panel 30 and/or base panel 14 may subjected to electret treatment such as, for example, DC corona discharge treatment. The coulombic force established on the exterior surfaces 16 and 36 of the panels 14 and 30, respectively, by the electret treatment enhances the ability of the exterior surfaces 16 and 36 to retain contaminants and prevent such contaminants from becoming airborne during opening of the peel pouch 10.

In a particular embodiment, the pouch of the present invention includes a non-dielectric base panel 14 and a dielectric cover panel 30 which has been subjected to DC corona discharge treatment. The cover panel 30 may be formed of a dielectric material such as, for example, a polyolefin. In such an embodiment, the cover panel 30 may be a transparent film. The base panel 14 may be formed of a cellulosic material such as Kraft paper, which is desired in selected applications due to its low cost. The cover panel 30 is electret treated with a DC corona charge apparatus (DC corona discharge treatment). The cover panel may be electret treated prior to sealing the base panel 14 to the cover panel 30, or the peel pouch 10 may be electret treated after sealing the base panel 14 to the cover panel 30. If this particular embodiment of the peel pouch 10 is electret treated, no charge will be formed on the base panel 14 as it is not formed of a dielectric material. When this peel pouch configuration is opened in the manner described above, the contaminants on the exterior surface 36 of the cover panel 30 are held to the exterior surface 36 by the attracting force established by electreting. The contaminants on the exterior surface 16 of the base panel 14 are not subjected to an attracting force, but are inhibited from becoming airborne as they are trapped between the surface 50 and the base panel 14. Thus, because this embodiment uses only one dielectric panel, it is particularly suited to opening in the manner described above to prevent airborne contaminants from the non-dielectric base panel from contacting the sterile article which was enclosed within the peel pouch 10.

In other embodiments, the base panel 14 may be made of a paper having a dielectric coating such as a polyolefin or polyolefin copolymer. The coating can be accomplished in a variety of ways, including through conventional emulsion coating techniques. For example, the emulsion coating can be accomplished by passing the paper through a nip formed by nip rollers with the nip being flooded by the dielectric emulsion. Those of skill in the art will readily recognize that the amount of dielectric emulsion applied to the paper can be easily and readily varied by condensing or diluting the emulsion. Additionally, this amount can be easily increased by passing the paper through the flooded nip two or more times since, with each passage, the paper tends to pick up more dielectric material.

In some desirable embodiments, the coated paper may be subjected to electreting in order to instill a charge on the dielectric coating. Electreting may be accomplished by, for example, application of a DC corona charge (DC corona discharge treatment) in a conventional manner. During electret treatment, the base panel 14 is charged and will assist in preventing the contaminants located on the exterior surface 16 of the base panel 14 from becoming airborne during opening of the peel pouch 10. In a similar manner, the cover panel 30 may also be formed of a non-dielectric material which is coated with a dielectric material and then subjected to electret treatment.

Although many configurations of the cover panel and base panel are suitable for use in the peel pack of the present invention, selected alternate configurations of the base panel 14 are shown in FIGS. 2 and 3. The base panel 14 depicted in FIG. 2 has a pair of tabs 22 and 24 on the right side of the peel pouch 10. The left side of the base panel 14 utilizes a single tab 22 extending outwardly from the edge 20. As also shown in FIG. 2, the tab and flap configuration may be positioned along more than one edge of the peel pouch.

The base panel 14 depicted in FIG. 3, which is a view of the exterior (or bottom) surface 16 of the base panel 14, does not utilize a tab extending from an edge, but rather the edge 20 of the base panel 14 simply extends outwardly beyond the edge 34 of the cover panel 30 (shown in dotted line). Each of the peel pouches depicted in FIGS. 2 and 3 illustrate configurations of the base and cover panels which may be opened in the manner described above.

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

I claim:

1. A peel pouch for enclosing articles to be sterilized, the peel pouch comprising:
    a base panel having an exterior surface and two flaps extending outwardly from the base panel;
    a cover panel overlying the base panel, the cover panel having a centerline and at least one tab disposed proximate to the centerline of the cover panel; and
    at least one seal joining the cover panel to the base panel so that a pouch is formed, the tab of the cover panel being positioned substantially between the flaps of the base panel;
    wherein at least a portion of the peel pouch is electret treated.

2. The peel pouch of claim 1 wherein the cover panel comprises a dielectric material.

3. The peel pouch of claim 2 wherein the dielectric material is selected from the group comprising polyolefins, polyesters and nylon.

4. The peel pouch of claim 3 wherein the dielectric material is a polyolefin.

5. The peel pouch of claim 2 wherein the cover panel is electret treated.

6. The peel pouch of claim 1 wherein the base panel comprises a cellulosic material.

7. The peel pouch of claim 6 wherein the base panel comprises paper.

8. The peel pouch of claim 7 wherein the base panel comprises Kraft paper.

9. The peel pouch of claim 6 wherein the cellulosic material is coated with a dielectric material.

10. A peel pouch adapted to enclose an article to be sterilized, the peel pouch comprising:
    a base panel having
        an exterior surface,
        an edge,
        a first and a second flap, the flaps being disposed along the edge of the base panel;
    a cover panel having at least one tab disposed on an edge of the cover panel, the cover panel overlying the base panel, the tab being disposed above and substantially between the first and second flaps; and
    at least one seal joining the cover panel to the base panel so that a pocket suitable to receive articles to be sterilized is formed;
    wherein, during separation of the cover panel from the base panel, the base panel is held securely while a separating force is applied to the tab of the cover panel to separate the cover panel from the base panel.

11. The peel pouch of claim 10 wherein the cover panel comprises a dielectric material.

12. The peel pouch of claim 11 wherein the cover panel is electret treated.

13. The peel pouch of claim 10 wherein the base panel comprises a dielectric material.

14. The peel pouch of claim 13 wherein the base panel is electret treated.

15. A peel pouch adapted to enclose an article to be sterilized, the peel pouch comprising:
    a base panel having an interior surface, an exterior surface, an edge, and a first and second flap disposed along the edge of the base panel; and
    a cover panel having an interior surface, an edge, and a tab disposed along the edge of the cover panel, the cover panel overlaying the base panel so that the interior surface of the base panel is adjacent to the interior surface of the cover panel, the tab of the cover panel being positioned substantially between the first and second flaps of the base panel;
    wherein, during separation of the cover panel from the base panel, the base panel may be held by applying a securing force to the first and second flaps of the base panel while a separating force is applied to the tab of the cover panel to separate the cover panel from the base panel.

16. The peel pouch of claim 15 wherein the cover panel comprises a dielectric material.

17. The peel pouch of claim 16 wherein the cover panel is electret treated.

18. The peel pouch of claim 15 wherein the base panel comprises a dielectric material.

19. The peel pouch of claim 18 wherein the base panel is electret treated.

* * * * *